(12) United States Patent
Smits et al.

(10) Patent No.: US 8,187,256 B2
(45) Date of Patent: May 29, 2012

(54) TATTOO REMOVAL AND OTHER DERMATOLOGICAL TREATMENTS USING MULTI-PHOTON PROCESSING

(76) Inventors: Alexander J Smits, Princeton, NJ (US); Szymon Suckewer, Princeton, NJ (US)

( * ) Notice: Subject to any disclaimer, the term of this patent is extended or adjusted under 35 U.S.C. 154(b) by 1004 days.

(21) Appl. No.: 12/136,943

(22) Filed: Jun. 11, 2008

(65) Prior Publication Data
US 2009/0149843 A1    Jun. 11, 2009

Related U.S. Application Data

(60) Provisional application No. 60/944,338, filed on Jun. 15, 2007.

(51) Int. Cl.
*A61B 18/20* (2006.01)
(52) U.S. Cl. .................. 606/9; 607/87; 128/898
(58) Field of Classification Search ........ 606/9; 607/88; 128/898
See application file for complete search history.

(56) References Cited

U.S. PATENT DOCUMENTS

| | | | |
|---|---|---|---|
| 2008/0154248 A1* | 6/2008 | Dunki-Jacobs | 606/9 |
| 2009/0227994 A1* | 9/2009 | Grundfest et al. | 606/9 |
| 2010/0082019 A1* | 4/2010 | Neev | 606/9 |

\* cited by examiner

*Primary Examiner* — Henry M Johnson, III
*Assistant Examiner* — Jeffrey Lipitz

(57) ABSTRACT

A system and method for providing multi-photon processing treatment to a patient. A localized, multi-photon processing event is initiated within a vicinity of an unwanted pigment in order to remove the pigment. The multi-photon processing event requires a relatively low energy, but very intense, pulse of light. The low amount of energy per pulse allows ablation of the material to be highly localized, with negligible thermal damage to surrounding material. The multi-photon event may be initiated by focusing a suitable electromagnetic pulse, such as a 2 mJ laser pulse having a 100 to 300 femtoseconds pulse duration, into a focal volume small enough that the intensity exceeds $10^{11}$ Watts/cm2. A suitably configured Ti:Sapphire solid state laser may provide such pulses at 1-10 kHz. By repeating the multi-photon processing event along the location of a tattoo, the tattoo may be removed with no damage to the surrounding tissue.

6 Claims, 2 Drawing Sheets

TATTOO REMOVAL AND OTHER DERMATOLOGICAL TREATMENTS USING MULTI-PHOTON PROCESSING

CROSS REFERENCE TO RELATED APPLICATIONS

This application is related to, and claims priority from, U.S. Provisional Patent application No. 60/944,388 filed on Jun. 15, 2007 by Smits et al entitled "Tattoo Removal and other Dermatological Treatment using Multi-photon processing" and to U.S. Provisional Patent application No. 60/953,826 filed on Aug. 15, 2007 by Smits et al entitled "Tattoo Removal and other Dermatological Treatment using Multi-photon processing" the entire contents of both of which are hereby incorporated by reference.

FIELD OF THE INVENTION

The present invention relates to systems and methods for dermatological treatment using multi-photon processing, and more particularly to systems and methods for tattoo or blemish removal using low energy (~2 mJ per pulse) focused, femtosecond (fsec) laser light pulses.

BACKGROUND OF THE INVENTION

Tattooing is a well-known and wide spread practice of marking or decorating human skin that is accomplished by injecting colored pigment into small deep holes made in the skin. Tattoos may have a wide range of colors and are relatively permanent. At estimated 25 million people in the United States have at least one such permanent tattoo, and with the current popularity of "body art", estimates are that over 250,000 women are being tattooed each year. The average age of people procuring a tattoo is approximately 18 years. These tattoos acquired in youth often become an embarrassment in later life as, in general, tattoos are not well received by the public and often create a barrier to employment or social acceptance. There is, therefore, a significant demand for the removal of tattoos.

Tattoo removal, however, is not easily accomplished. In tattooing, pigments are injected into the dermis. This is the layer of skin that lies immediately beneath the approximately one mm thick epidermis, which is the dead, external surface layer of the skin. The injected pigments initially tend to aggregate in the upper dermis, close to the epidermis. Physical removal of tattoos, therefore, requires abrading away the entire epidermis immediately above the tattoo pigment. This may be a painful process and may leave the subject with significant scarring. Over time, the tattoo pigments may become encapsulated in fibroblasts and migrate deeper into the dermis so that older tattoos, while a little duller, are even more difficult to remove by abrasion.

With the advent of high power lasers, an alternative, non-abrading method of removing tattoos that relies on thermal photoablation has become possible. In tattoo removal based on thermal photoablation, the laser wavelength is chosen so that the tattoo pigment absorbs the laser light more readily than the surrounding skin does. The laser pulses are then made powerful enough so that the pigment heats up sufficiently to thermally photoablate, i.e., to dissociate into small fragments. These fragments are typically no longer colored and may be also transported out of the dermis by macrophages or diffusion.

Tattoo pigments, however, cover a range of colors, including black, white, blue, red, green, and others. Dark blue-black amateur and professional tattoos usually contain amorphous carbon, graphite, India ink, and organo-metallic dyes. There is, therefore, no one laser most suitable for tattoo removal by thermal photoablation.

Tattoo removal is, therefore, currently accomplished using a variety of lasers to induce thermal photo-ablation including, but not limited to, Q-switched Nd:Yag lasers typically operating at 1064 nanometer (nm) or 532 nm, with 5-20 nanosecond (nsec) pulse duration, Q-switched Alexandrite lasers typically operating at 755 nm, with 100 nsec pulse duration, and Q-switched Ruby lasers typically operating at 694 nm, with 20-40 nsec pulse duration.

All these lasers, collectively known as nsec-type lasers, may be employed in a similar manner to remove tattoos. Typically, a cream to numb the skin is applied to the patient prior to the treatment to reduce the level of pain felt during the treatment. Short pulses of the laser light, typically of the order of 5 to 100 nsec, are then directed through the surface of the subject's skin and are absorbed by the tattoo pigment. The light breaks the pigment into particles by thermal photoablation. The particles are small enough to be absorbed by the body.

The principal sources of trauma in the nsec laser treatment of tattoos are the heating of the skin, which causes damage similar to a second-degree burn, and the formation of highly localized shock waves in the dermis that cause undesirable tissue damage. After the treatment, the body's scavenger cells remove the particles of pigment from the treated pigmented areas. The skin and tissue damage then heals over the next several weeks. More then one treatment is usually necessary to remove the entire tattoo. Some scarring or color variations are likely to remain. Healing time varies depending upon the size and depth of the tattoo, the procedure used and the patient's healing process.

All the current laser procedures for tattoo removal are painful, expensive, rarely 100% effective, may leave permanent scarring and typically require multiple treatments spread over a period of time.

What is needed is a tattoo removal system and method that is more effective than the existing methods, does not leave permanent scarring and is preferably not painful and can be accomplished in a single treatment.

SUMMARY OF THE INVENTION

Briefly described, the present invention provides a system and method for providing multi-photon processing treatment to a patient.

In a preferred embodiment of the invention, a location of a pigment on or within the patient is determined. The pigment may, for instance, be a tattoo pigment of an unwanted tattoo, or it may be some the pigment of a blemish or a pigment associated with some unwanted growth such as, but not limited to, a carcinoma or a wart. A localized, multi-photon processing event is then initiated within a vicinity of the unwanted pigment in order to remove the pigment.

A localized, multi-photon processing event is an event in which a large number of photons—at least 5-10, and typically 100 or more—are absorbed simultaneously by a molecule or material. Such multi-photon processing events require very intense light, i.e., many photons in a small volume at the same time. Multi-photon processing events, however, do not necessary require much energy per pulse. The multi-photon processing events may result in the dissociation of the absorbing molecule or material. This photoablation, however, differs from thermal photoablation in that the low amount of energy per pulse involved allows the process to be very localized, and may result in no or negligible thermal heating or shocking of any surrounding material. A localized, multi-photon event may, for instance, be initiated by focusing suitable pulses of electromagnetic radiation. For instance, by focusing a 2 mJ pulse of laser light that has a temporal pulse length in the range from 100 to 300 femtoseconds in duration to a small enough focal volume that the intensity is equal to or greater than $10^{11}$ Watts/cm$^2$, a multi-photon processing event may be initiated. Such pulses may be obtained from, for instance, a suitably configured Titanium doped Sapphire (Ti:Sapphire) solid state laser.

By using a high-repetition rate femtosecond laser, and repeating the localized, multi-photon processing event initializing along the location of the pigment in, for instance, a tattoo, the entire tattoo may be removed with little or no damage to the surrounding tissue. This process may be accomplished manually, or under the guidance of a computer, or through a combination thereof.

These and other features of the invention will be more fully understood by references to the following drawings.

DETAILED DESCRIPTION

Figure 1:
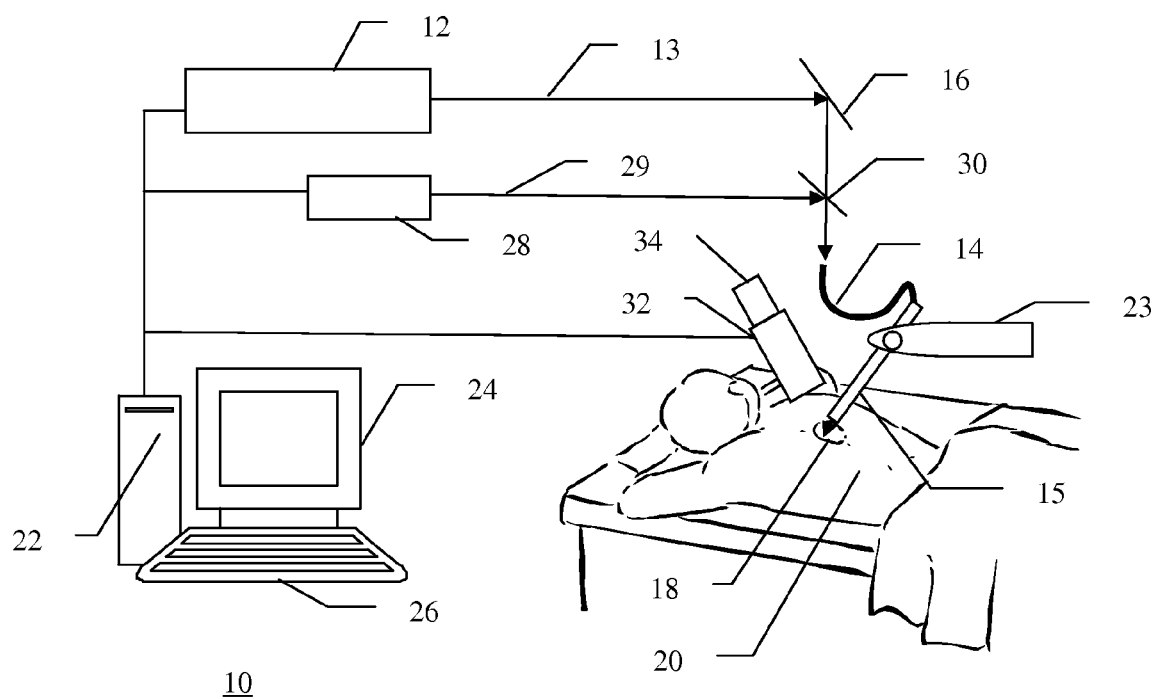
FIG. 1 is a schematic drawing of an exemplary apparatus of the present invention for providing multi-photon processing treatment.

The present invention relates to systems and methods for dermatological treatment using multi-photon processing events. In particular, the present invention is directed to systems and methods for tattoo or blemish removal using low power (~2 mJ per pulse) focused, femtosecond laser light pulses to initiate multi-photon processing events.

As described above, the laser light currently used in procedures for tattoo removal typically interacts with the pigments in the skin through a thermal photo-ablation process (also called a thermal ablation process). This thermal photoablation process occurs when the laser pulses have a relatively high energy but a low intensity. As each pulse has a low density of photons, only single photons are absorbed in any given absorption event. Each absorption event supplies some heat to the pigment. By having enough of these absorption events occur before the heat can be dissipated, the pigment material may be heated to a high enough temperature that the pigment undergoes thermal photoablation, i.e., the pigment dissociates into particles small enough to be absorbed by the body. After the thermal photo-dissociation of the pigment, the accumulated heat diffuses out of the focal region, causing undesirable heating, and possibly burning, of the surrounding skin. The diffusing heat may, for instance, cause trauma similar to a second-degree burn in the vicinity of the treatment. In addition, the small volume of rapidly heated material may also expand rapidly, generating highly localized shock waves in the dermis that may also cause undesirable tissue damage.

When the intensity of the laser pulses is greatly increased, however, the photoablation of materials changes to what is called a "multi-photon" process. This is not a thermal process. In a very high-intensity laser pulse, the density of photons is so great that during a single absorption event, many photons are absorbed simultaneously. The number of photons absorbed simultaneously by the material in multi-photon ablation may be 10-100 photons or more per molecule or atom (per few molecules or few atoms). The density of photons in a pulse is so high that number of photons absorbed simultaneously is very large, hence photoablation may occur even though the energy of the pulse is 2 mJ or less. This amount of energy is sufficiently low that little or no damaging thermal heating of the surrounding tissue occurs as the energy diffuses out. This is in marked contrast to thermal ablation with low-intensity pulsed lasers where only a single photon is absorbed in any given absorption event, and the pulse energy necessary for photoablation is sufficiently high that damaging heating of the surrounding tissue occurs as the heat diffuse out.

"Few photon processes", i.e., processes that involve not more than 3 photons in a single absorption event, also tend to result in thermal ablation, even though few-photon processes are sometimes inaccurately labeled "multi-photon processes" in some literature.

For a multi-photon process, or multi-photon photoablation, to be useful for treating skin discolorations and tattoos, the intensity of the laser pulses needs to be sufficiently high. At the same time, the energy content of each pulse needs to be sufficiently low to avoid undesirable heating and shock wave effects. One way to simultaneously achieve both the high intensity and low energy is by using ultra-short laser pulses. In laser physics, ultra-short pulses are typically defined to be pulses up to 10 psec in duration, although some time pulses as long as 200 psec are termed ultra-short. For effective multi-photon processing, a pulse duration in the range of 100 to 300 fsec is preferred, where 1 fsec is equal to $10^{-15}$ sec. These ultra-short pulses are significantly shorter than those produced by n-sec type lasers. For instance, a 10 nsec laser pulse is 100,000 times longer than a 100 fsec laser pulse.

In addition to avoiding the heating of surrounding tissue, the multi-photon ablation process is practically independent of the pigment color as the process does not depend on differential absorption by the pigment. Using multi-photon processing to remove pigment from the skin does not, therefore, require using different laser wavelengths for different pigments. This is in sharp contrast to thermal photoablation processes where the wavelength needs to be chosen carefully to maximize the interaction with the specific pigment, or pigments, used in the tattoo, while allowing for sufficient dermal penetration to reach the pigment and at the same time avoiding absorption in the natural skin pigment, the melanin.

In multi-photon ablation, the ablation rate for any pigmented material at a given spot is typically only a function of the number of laser pulses, i.e., the total energy, and does not, typically, depend on the wavelength of the pulse.

Moreover, the multi-photon process of this invention is readily directed below the skin with sufficient intensity and is independent of the laser wavelength, in contrast with current methods that use thermal photoablation.

Furthermore, in the present invention, high intensities on target are easily achieved. As the laser wavelengths typically used to initiate multi-photon processing events are in the infra-red, they can penetrate deep into the dermis. The necessary high intensities on target may therefore be accomplished by using, for instance, a short focal length lens to focus the laser directly on the pigment below the skin. In addition, the focal volume can be made very small and typically less than 50 µm in diameter and depth. By adjusting the laser power and pulse duration, the intensity within the focal volume can be made to exceed the threshold intensity necessary for multi-photon processing while the intensity near the skin surface may be kept too low for multi-photon processing to occur. In this way, the pigment may be multi-photon ablated while the surface of the skin is undamaged.

A preferred embodiment of the invention will now be described in detail by reference to the accompanying drawings in which, as far as possible, like elements are designated by like numbers.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

FIG. 1 is a schematic drawing of an exemplary apparatus of the present invention for providing multi-photon processing treatment. The multi-photon processing treatment apparatus 10 may include a femtosecond laser 12, a fiber optic 14, a delivery optic 16, a delivery wand 15, a positioning unit 23, a control computer 22 having a viewing monitor 24 and an input device 26, a guidance light source 28, a mixing optic 30, a telescope 32 and a camera 34. The input device 26 may, for instance, be a keyboard, a touch screen, a mouse, a tablet or any other suitable computer input device.

The femtosecond laser 12, for instance, may be a suitably configured Titanium doped sapphire (Ti:Sapphire) solid state laser as supplied by, for instance, Del Mar Photonics of Del Mar, Calif. Such a laser may be configured to be a tunable laser operating over a broad range of near infra-red wavelengths centered at 800 μm, and emitting femtosecond pulses 13 having pulses with a temporal duration in the range of 100 to 300 femtoseconds, a pulse energy of 0.5-2 mJ per pulse and a repetition rate of 1-10 kHz. As one skilled in the art will realize, such a laser may be operated to reasonable effect with pulses as long as 200 psec in duration. 200 psec pulse would, however, require significantly higher energy per pulse than for 100 fsec pulses. Pulses that are shorter than 200 psec are typically better for initiating multi-photon processing events, and pulses in the range 100 to 300 femtoseconds are preferred. For such ultrashort, high repetition rate pulse lasers with pulse durations in the range 100 fsec up to 10 psec, the total procedure time for treating a 1 cm$^2$ tattoo is expected to take only several minutes.

The femtosecond laser 12 may also or instead be a suitably configured laser made using Cr doped Forsterite, or Er- and Yb-doped fibers, or some combination thereof.

The femtosecond pulses 13 may be transmitted to the area of interest 18 on the patient 20 via a delivery optic 16, a fiber optic 14 and a delivery wand 15. The delivery optic 16 may, for instance, be a flat or focusing mirror used to direct the femtosecond pulses 13 into the fiber optic 14. The fiber optic 14 may, for instance, be any glass or plastic fiber having the requisite transparency to the femtosecond pulses 13. The fiber optic 14 may be used to transport the femtosecond pulses 13 to the delivery wand 15. The delivery wand 15 may be operated by hand, or may be supported by a positioning unit 23 that may be under the control of a control computer 22.

The delivery wand 15 may also deliver a guidance light beam 29. The mixing optic 30 may assist in delivering the guidance light beam 29 to the fiber optic 14 or the delivery wand 15. The mixing optic 30 may, for instance, be a suitable multilayer mirror that reflects the guidance light beam 29 but is transparent to the femtosecond pulses 13. The guidance light beam 29 may, for instance, be from a Helium Neon laser, although any other laser with an output in the visible spectrum would be suitable. The guidance light source 28 may include a detector for monitoring how much of the guidance light beam 29 is reflected back from the surface of the patient 20. In this way a feed-back loop may be established to monitor the distance between a focusing tip of the delivery wand 15 and the patient 20.

Figure 2:
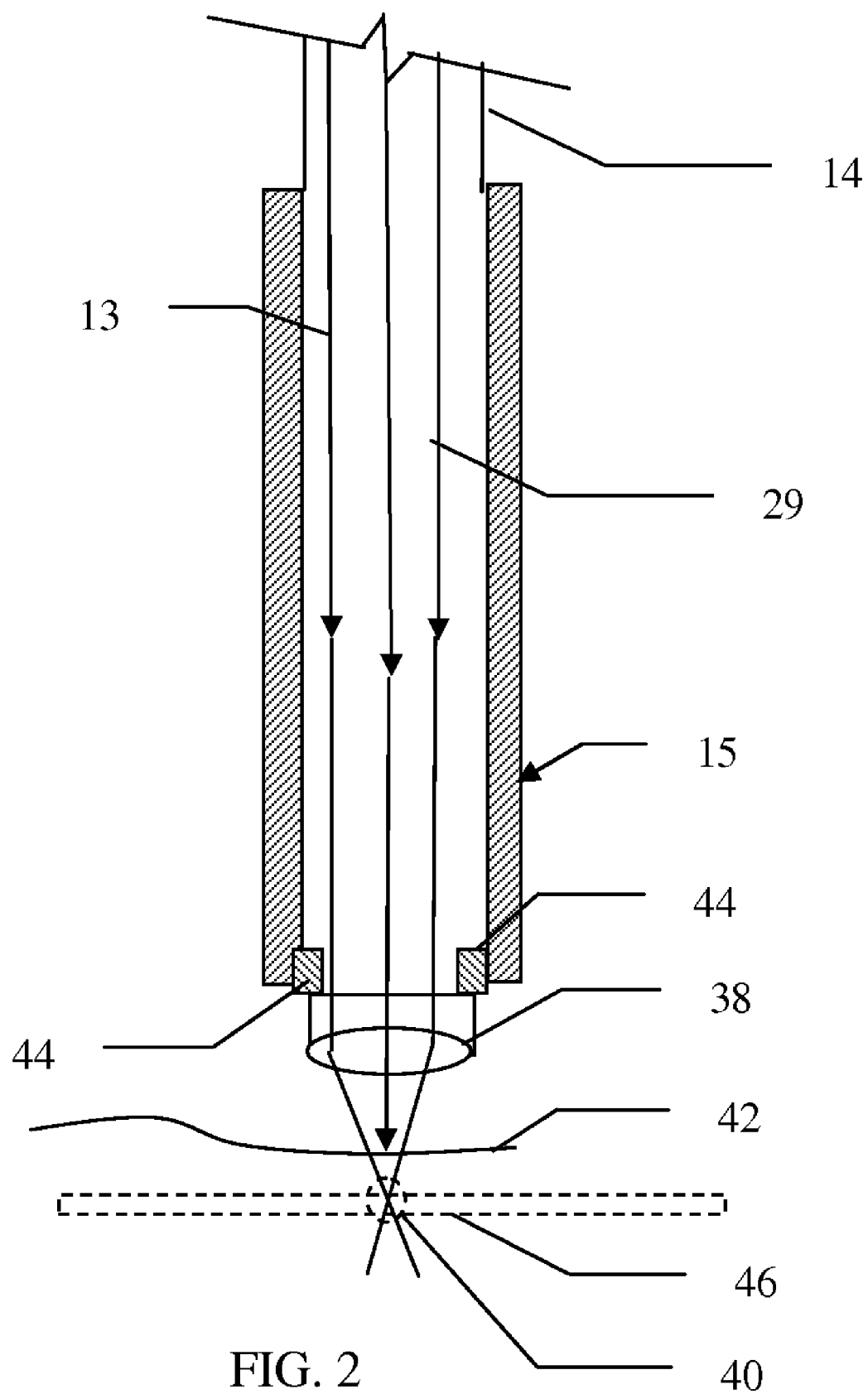
FIG. 2 is a cross-sectional drawing of an exemplary delivery wand of the present invention for providing multi-photon processing treatment.

FIG. 2 is a cross-sectional drawing of an exemplary delivery wand 15 of the present invention for providing multi-photon processing treatment. The delivery wand 15 may include a short focal length lens 38, one or more micro-positioning elements 44 and a fiber optic 14. The fiber optic 14 may deliver the femtosecond pulses 13 and the guidance light beam 29 to the short focal length lens 38. The short focal length lens 38 focuses the femtosecond pulses 13 to a focal volume 40 that is positioned beneath a surface of the patent 42 in the vicinity of the pigmented layer 46. The pigmented layer 46 is typically located about 1 to 2 mm beneath the surface of the patent 42.

The focal volume 40 may be 500 μm in diameter or smaller. In a preferred embodiment, the focal volume 40 may be made substantially equal to the thickness of the pigmented layer 46 that may be as small as 5 μm.

The power density in the focal volume 40 typically needs to be in the range of $10^{12}$-$10^{13}$ Watts/cm$^2$ in order to initiate a multi-photon processing event. With very long wavelength lasers such as, but not limited to, the 10 μm wavelength $CO_2$ laser, multi-photon processing events may be initiated when the power density in the focal volume 40 is in the range of $10^{11}$ Watts/cm$^2$.

The delivery wand 15 may also deliver a guidance light beam 29 that may be a Helium Neon laser beam or some other suitable visible light laser. A portion of the guidance light beam 29 may be reflected off the surface of the patent 42 and back up the delivery wand 15. This reflected portion of the guidance light beam 29 may be detected by, for instance, a suitably located photo-diode. The reflected portion of the guidance light beam 29 may then be used as a feed back loop and used to control the location of the focal volume 40 relative to the surface of the patent 42 using the micro-positioning elements 44. The micro-positioning elements 44 may, for instance, be piezoelectric devices, or they may be MEMS actuated devices or they may be micro-mechanical devices controlled by, for instance, electric motors.

EXAMPLES OF USE OF THE INVENTION

Example 1

The use of multi-photon processing to remove tattoos has been demonstrated using a pulsed Ti:Sapphire laser with a pulse duration of approximately 100 fsec. A frozen pig foot obtained from a butcher was thawed and a three color tattoo was laid down on the skin (K & B Tattooing and Piercing, Hightstown, N.J.). The colors were red, green, and black, and the tattoo measured approximately 5 cm by 3 cm. Pig skin was chosen for the experiments because it is anatomically and physiologically very similar to human skin as detailed in, for instance, the article published by Sullivan et al entitled "The pig as a model for human wound healing." In Wound Repair Regen. (2):66-76, 2001, the contents of which are hereby incorporated by reference. This 100 fsec, 1 mJ per pulse laser operating at 10 Hz repetition rate was focused at a point about 100 to 200 μm below the surface of the skin. A patch of green dye was then treated. Similar results were obtained on red dye and black dye, demonstrating that this particular broadband laser was effective on all dyes tested here.

Example 2

The use of multi-photon processing to remove tattoos has also been demonstrated using pulsed Ti:Sapphire laser with a pulse duration of about 10 psec. A frozen pig foot obtained from a butcher was thawed and a six color tattoo was laid down on the skin (K & B Tattooing and Piercing, Hightstown, N.J.). The colors were red, green, blue, orange, yellow and black, and the tattoo measured approximately 5 cm by 3 cm. The laser used had an energy of ~10 mJ per pulse and was run at a 10 Hz repetition rate. The laser was focused at a point about 100 to 200 µm below the surface of the skin. A section containing all colors of the tattoo was then treated. The eradication of all dyes using this 10 psec laser was clearly evident, although not as good as with 100 fsec laser.

Example 3

The multi-photon processing to remove tattoos was contrasted with photo-thermal ablation removal of tattoos by using a nsec-type laser with a pulse duration of about 10 nsec to remove a different section of the same tattoo described in Example 2. The 5 nsec, 200 mJ/pulse Nd:YAG laser was focused at a point about 100 to 200 µm below the surface of the skin. The eradication of the some of the dyes was clearly evident, but some dyes were not removed because the wavelength of the laser (1.064 µm) was not a good match to the dye. Importantly, when enough laser energy was used to remove the tattoo, the heating of the skin was intense and the skin damage was severe, and sections of the skin were severely burnt. The contrast with the treatments using ultrashort laser pulses (Examples 1 and 2) was dramatic.

The multi-photon processing system and method of the present invention, described and demonstrated above, permits the fast and complete removal of tattoo pigments in the skin and other skin discolorations with virtually no pain or scar formation using multi-photon processing. The multi-photon processing system and method also permits dermatological procedures, including cosmetic procedures such as, but not limited to, the removal of blemishes, liver spots, warts, acne, basal-cell-carcinoma, cutaneous T-cell lymphoma or eczema, the treatment and mitigation of facial scarring, and can be used in the processes of exfoliation and dermabrasion. The effectiveness of the multi-photon photoablation procedure is virtually independent of the laser wavelength. Therefore the particular wavelength and bandwidth of the laser pulses used may cover a very wide range. The wavelength can range from 0.2 µm to 10 µm, but it can be as short as 0.11 µm and as long as 100 µm, but is preferably in the range from 0.25 µm to 1.06 µm. The bandwidth can range from 10 GHz to 10 THz (where 1 GHz is $10^9$ Hz, and 1 THz is $10^{12}$ Hz), but it can be as small as 1 GHz and as large as 100 THz.

A clinical use of the multi-photon processing system and method may proceed as follows. In a preliminary examination, a tattoo may first be evaluated in terms of the extent of the affected region, the depth of the dye layer, and the types of dyes used in the tattoo. Other factors, such as the natural skin color surrounding the tattoo, the age of the patient, the quality of natural wound healing, and other factors including the patient's general health may be noted. If it is decided to proceed with the tattoo removal, the area where the tattoo is located may be held firmly and securely in a comfortable position. A precise map of the tattoo may then be created from a white light image of the tattoo obtained by, for instance, a camera 34, that may be a CCD camera, and the imaging telescope 32 operating under the control of the control computer 22. Using image processing techniques, details of the physical location of the tattoo pigments may be obtained, including the depth of the pigmented layers. Using these parameters, a patient-specific procedure may be devised for the tattoo removal using a suitable software program. This computer-generated procedure may include calculating the necessary laser parameters such as, but not limited to, the power per shot, the number of shots, the repetition rate, the positioning and the focusing requirements of the laser beam, the shot pattern and the specific instructions for the laser positioning system.

In a manual treatment, the operator may choose the laser parameters from the recommendations given in the computer-generated procedure. The operator may then apply the laser pulses to the area of area of interest 18 being treated using the specially designed delivery wand 15. Progress may be monitored either by direct visual inspection, or by the use of a camera 34 that may connected to a viewing monitor 24 by means of the control computer 22.

In a computer-controlled treatment, the delivery wand 15 may be directed to the area by a laser positioning system that may be part of the positioning unit 23. The operator may monitor progress either by direct visual inspection or by the use of the camera 34 connected to the viewing monitor 24. The camera may also be used in all treatments, manual or computer-controlled to obtain and store still or video images to record the progress of the removal procedure. As multi-photon processing uses ultra-short pulsed lasers, where ultra-short pulses are pulses up to 10 psec in duration, and in some cases up to 200 psec in duration, although the preferred pulse duration for such processing is in the range of 100 to 300 fsec, for which the beam energy may be in range of 0.5-2 mJ per pulse with laser repetition rate of around 1-10 kHz. For such ultra-short, high repetition rate pulse lasers with pulse durations in the range 100-300 fsec, the total procedure time for treating a 1 $cm^2$ tattoo is expected to take only several minutes.

The laser pulses are transmitted to the area of interest 18 to be treated by a delivery wand 15 that is typically connected to the femtosecond laser 12 using fiber optics. The delivery wand 15 may be operated manually or via the control computer 22 using a computer-controlled positioning system. The delivery wand 15 may house a short focal length lens 38 to focus the laser pulses below the skin at the depth of the pigmented layer 46 comprising the tattoo. The wand may also output a second laser beam that is a guidance light beam 29. The guidance light beam 29 may, for instance be a helium-neon laser although any other laser with an output in the visible spectrum would be suitable. The second laser beam provides a signal that can be used to monitor the distance between the delivery wand 15 and the surface of the skin 42. The guidance light beam 29 may also be used to infer the distance from the short focal length lens 38 to the pigmented layer 46 comprising the tattoo. This signal may be used to generate a feedback control output that will shut off the femtosecond laser pulses 13 when one or both of these distances exceed some minimum and maximum limits. For instance, the femtosecond pulses 13 may be blocked by, for instance the delivery optic 16 if the distance from a front surface of the short focal length lens 38 to the pigmented layer 46 is, for instance, greater than 2 mm, or is outside a range of 0.5 to 2.5 mm. These limits are set to prevent undesirable interactions of the laser with tissue outside the pigmented layers comprising the tattoo, and also to ensure operator safety. The second laser beam can also be used to illuminate the area of interest 18 being treated, although other light sources may be used instead of or in addition to the laser illumination.

Alternatively, the distance from the operating tip of the delivery wand 15 to the pigmented layer 46 comprising the tattoo may be set by an optically transparent spacer sheet.

In a further embodiment of the invention, the thickness of this optically transparent spacer sheet may be set by prior visual or computer inspection of the tattoo. The spacer sheet may be positioned on the skin surface over the area to be treated, and the wand may then move over the area to be treated while maintaining contact with the spacer sheet.

The treated area may be evaluated after one round of laser ablation. A further treatment may be advised, either immediately following the first treatment, or after one or more days. Based on experiments 1 and 2 described above, it is expected that most individuals may only need a single treatment.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

What is claimed is:

1. A method of removing a portion of a tattoo, said method comprising the steps of:
providing a device capable of generating a pulse of electromagnetic radiation having a temporal pulse length that is controllable by hardware comprising a programmed computer, to be in the range of 100 to 300 femtoseconds in duration and have a bandwidth in a range of 10 GHz to 100 THz;
locating a position of a pigment defining said portion of said tattoo on or within a dermal layer of said patient;
providing a focusing element comprising at least one lens, to focus said pulse of electromagnetic radiation to a focal volume having a diameter less than the thickness of said dermal layer containing said pigment and to an intensity that is equal to or greater than $10^{11}$ Watts/cm;
positioning, comprising using said programmed computer, said focusing element such that said focal volume will occur in a range of 10 μm to 2000 μm below an upper surface of said dermal layer containing said pigment; and
initiating, comprising using said programmed computer, generation of said pulse of electromagnetic radiation by said device, thereby producing a localized, multi-photon process event in or within a vicinity of said pigment causing molecules of said pigment to dissociate and no longer appear colored.

2. The method of claim 1 wherein said pulse of electromagnetic radiation has an energy that is equal to or less than 2 milli-Joules.

3. The method of claim 1 wherein said focal volume is equal to or less than 500 μm in diameter.

4. The method of claim 1 further comprising repeating initiating said localized, multi-photon processing event until said pigment is removed.

5. The method of claim 1 wherein said pulse of electromagnetic radiation has a temporal pulse length that is substantially equal to 100 femtoseconds in duration and said predetermined threshold is substantially equal to $10^{11}$ Watts/$cm^2$.

6. The method of claim 1 further comprising the step of preventing, by said computer using a feed-back signal from a second, visible light laser as a guidance beam, the initiation of said localized, multi-photon processing event unless said lens is located such that said focal volume will occur in said range of 10 μm to 2000 μm below said upper surface.

* * * * *